US009345774B2

(12) United States Patent  (10) Patent No.: US 9,345,774 B2
Petersson et al.  (45) Date of Patent: May 24, 2016

(54) TOPICAL COMPOSITION COMPRISING A FILM-FORMING POLYMER FOR DELIVERING AN ACTIVE INGREDIENT TO SKIN

(71) Applicant: LEO PHARMA A/S, Ballerup (DK)

(72) Inventors: Karsten Petersson, Ballerup (DK); Kit Frederiksen, Copenhagen Ø (DK); Diana Omkvist, Ballerup (DK); Jörgen Jansson, Ballerup (DK)

(73) Assignee: LEO PHARMA A/S, Ballerup (DK)

( * ) Notice: Subject to any disclaimer, the term of this patent is extended or adjusted under 35 U.S.C. 154(b) by 0 days.

(21) Appl. No.: 14/412,978

(22) PCT Filed: Jul. 5, 2013

(86) PCT No.: PCT/EP2013/064300
§ 371 (c)(1),
(2) Date: Jan. 5, 2015

(87) PCT Pub. No.: WO2014/006201
PCT Pub. Date: Jan. 9, 2014

(65) Prior Publication Data
US 2015/0157729 A1  Jun. 11, 2015

Related U.S. Application Data

(60) Provisional application No. 61/668,846, filed on Jul. 6, 2012.

(51) Int. Cl.
*A61K 9/00* (2006.01)
*A61K 47/32* (2006.01)
(Continued)

(52) U.S. Cl.
CPC ............... *A61K 47/32* (2013.01); *A61K 9/0014* (2013.01); *A61K 9/124* (2013.01); *A61K 9/7015* (2013.01);
(Continued)

(58) Field of Classification Search
CPC ....................................................... A61K 47/32
See application file for complete search history.

(56) References Cited

U.S. PATENT DOCUMENTS

2004/0213744 A1  10/2004  Lulla et al.
2005/0276842 A1  12/2005  Zhang et al.
(Continued)

FOREIGN PATENT DOCUMENTS

EP  0521455 A2  1/1993
EP  0515312 B1  8/1996
(Continued)

OTHER PUBLICATIONS

International Preliminary Report on Patentability and International Preliminary Examining Authority for PCT/EP2013/064300 mailed on Oct. 23, 2014.
(Continued)

*Primary Examiner* — Paul Dickinson
(74) *Attorney, Agent, or Firm* — Birch, Stewart, Kolasch & Birch, LLP (57) ABSTRACT

A sprayable film-forming pharmaceutical composition for dermal application comprises at least one therapeutically active ingredient dissolved in a pharmaceutically acceptable propellant selected from the group consisting of dimethyl ether, diethyl ether and methylethylether, and a mixture of dimethyl ether, diethylether and methylethyl ether, and a second propellant selected from $C_{3-5}$ alkanes, hydrofluoroalkanes, hydrochloroalkanes, fluoroalkanes and chlorofluoroalkanes, the propellant being present in an amount of 50-99.5% w/w of the composition, the composition further comprising a film-forming polymer, a plasticizer and an oily release-enhancing agent.

20 Claims, 6 Drawing Sheets

(51) Int. Cl.
*A61K 9/70* (2006.01)
*A61K 9/12* (2006.01)
*A61K 31/573* (2006.01)
*A61K 47/06* (2006.01)
*A61K 47/08* (2006.01)
*A61K 47/10* (2006.01)
*A61K 47/14* (2006.01)
*A61K 47/38* (2006.01)
*A61K 47/44* (2006.01)
*B65D 83/14* (2006.01)
*A61K 47/22* (2006.01)

(52) U.S. Cl.
CPC .............. *A61K 31/573* (2013.01); *A61K 47/06* (2013.01); *A61K 47/08* (2013.01); *A61K 47/10* (2013.01); *A61K 47/14* (2013.01); *A61K 47/22* (2013.01); *A61K 47/38* (2013.01); *A61K 47/44* (2013.01); *B65D 83/752* (2013.01)

(56) References Cited

U.S. PATENT DOCUMENTS

| | | |
|---|---|---|
| 2007/0189977 A1 | 8/2007 | Zhang et al. |
| 2007/0189978 A1 | 8/2007 | Zhang et al. |
| 2007/0189980 A1 | 8/2007 | Zhang et al. |
| 2007/0190124 A1 | 8/2007 | Zhang et al. |
| 2007/0196293 A1 | 8/2007 | Zhang et al. |
| 2007/0196323 A1 | 8/2007 | Zhang et al. |
| 2007/0196325 A1 | 8/2007 | Zhang et al. |
| 2007/0196452 A1 | 8/2007 | Zhang et al. |
| 2007/0196453 A1 | 8/2007 | Zhang et al. |
| 2007/0196457 A1 | 8/2007 | Zhang et al. |
| 2007/0196458 A1 | 8/2007 | Zhang et al. |
| 2007/0196459 A1 | 8/2007 | Zhang et al. |
| 2007/0248658 A1 | 10/2007 | Zurdo Schroeder et al. |
| 2007/0280972 A1 | 12/2007 | Zhang et al. |
| 2008/0019927 A1 | 1/2008 | Zhang et al. |
| 2012/0294907 A1 | 11/2012 | Zhang et al. |
| 2012/0294926 A1 | 11/2012 | Zhang et al. |
| 2012/0301517 A1 | 11/2012 | Zhang et al. |
| 2013/0022564 A1 | 1/2013 | Zhang et al. |
| 2014/0314815 A1 | 10/2014 | Zhang et al. |

FOREIGN PATENT DOCUMENTS

| | | |
|---|---|---|
| WO | WO 00/45795 A2 | 8/2000 |
| WO | WO 2006/111426 A1 | 10/2006 |
| WO | WO 2007/031753 A2 | 3/2007 |
| WO | WO 2011/154004 A1 | 12/2011 |

OTHER PUBLICATIONS

International Search Report for PCT/EP2013/064300 mailed on Sep. 19, 2013.

Written Opinion of the International Searching Authority for PCT/EP2013/064300 mailed on Sep. 19, 2013.

TOPICAL COMPOSITION COMPRISING A FILM-FORMING POLYMER FOR DELIVERING AN ACTIVE INGREDIENT TO SKIN

CROSS REFERENCE TO RELATED APPLICATIONS

This application is the National Phase of PCT/EP2013/064300 filed on Jul.5, 2013, which claims priority under 35 U.S.C. 119(e) to U.S. Provisional Application No. 61/668,846 filed on Jul. 6, 2012, all of which are hereby expressly incorporated by reference into the present application.

FIELD OF INVENTION

The present invention relates to a sprayable pharmaceutical composition for application on skin and containing a film-forming polymer and at least one active ingredient, the composition forming a thin and transparent film on the skin on evaporation of a propellant.

BACKGROUND OF THE INVENTION

Human skin, in particular the outer layer, the stratum corneum, provides an effective barrier against penetration of microbial pathogens and toxic chemicals. While this property of skin is generally beneficial, it complicates the dermal administration of pharmaceuticals in that a large quantity, if not most, of an active ingredient applied on the skin of a patient suffering from a dermal disease may not penetrate into the viable layers of the skin where it exerts its activity. To ensure an adequate penetration of the active ingredient into the dermis and epidermis, it is generally preferred to include the active ingredient in a dissolved state, typically in the presence of a low-molecular volatile solvent such as an alcohol, e.g. ethanol, or a diol, e.g. propylene glycol, which may also act as a penetration enhancer for the active ingredient. Another way to obtain penetration of the active ingredient into the skin is to provide occlusion by formulating the active ingredient in a hydrophobic vehicle such as petrolatum. However, ointments containing petrolatum generally have a tacky or greasy feel that persists for quite some time after application, and are consequently not cosmetically acceptable.

As an alternative to conventional formulations such as ointments, compositions containing film-forming polymers in which an active ingredient has been incorporated have been developed. Film-forming compositions have mainly been used to provide transdermal delivery of an active ingredient such as in transdermal patches or, more recently, as film-forming solutions composed of a film-forming polymer, a plasticiser and a low-molecular volatile solvent for the active ingredient. When the solution is applied on skin, a thin polymeric film is formed after evaporation of the solvent.

EP 515 312 B1 discloses a topical formulation containing terbinafine as the active ingredient and a film-forming polymer, e.g. polyvinylacetate or acrylic and methacrylic acid ester copolymers, for use as a nail varnish in the treatment of onchomycosis.

WO 2006/111426 discloses a film-forming solution containing a vitamin D derivative and a corticosteroid for use as a nail varnish in the treatment of nail psoriasis. The film-forming polymer may be selected from polyvinylpyrrolidone, butyl ester of polyvinyl methyl ether and maleic acid copolymer and acrylate and ammonium methacrylate copolymer. The composition may contain ethanol as a solvent and may additionally contain a penetration enhancer.

US 2007/0248658 discloses compositions comprising film-forming polyurethanes or polyurethane and acrylate copolymers and one or more active ingredients for use in dermal or transdermal delivery of the active ingredient(s) such as ethinylestradiol. The composition may additionally contain a low-molecular volatile solvent such as ethanol or isopropanol and a penetration enhancer such as oleic acid, oleyl alcohol, propylene glycol propylene carbonate, N-methylpyrrolidone and isopropyl myristate.

US 2004/0213744 discloses a sprayable composition for topical application comprising a film-forming polymer, a permeation enhancer, a solubilizer, a plasticizer and an active ingredient. The film-forming polymer may be an acrylic polymer or copolymer, a methacrylic acid polymer or copolymer, polyvinylacetate, polyvinyl alcohol, polyvinylpyrrolidone or a cellulose polymer. The permeation enhancer may be selected from surfactants, oleic acid, mixed esters of capric and caprylic acid, polyhydric alcohols, isopropyl myristate etc. The solubilizer may be a surfactant, polyhydric alcohol or a copolymer of dimethylamine ethyl methacrylate and methacrylic acid ester copolymer. The plasticizer may be selected from triethyl citrate, dimethyl isosorbide, acetyl tributyl citrate, castor oil, propylene glycol etc. The composition may further include a propellant, e.g. hydrocarbon, hydrofluorocarbon, dimethylether, nitrogen, carbon dioxide, etc.

WO 2007/031753 discloses a film-forming composition comprising an active ingredient which is present in at least 80% saturation, a film-forming polymer such as polyvinylpyrrolidone, polyvinyl alcohol, acrylic polymers and copolymers, methacrylic polymers and copolymers and cellulose polymers, a low-molecular volatile solvent such as ethanol, a propellant such as hydrofluoroalkane, and preferably also an antinucleating agent such as polyvinyl alcohol and a plasticizer such as glycerol, polyethylene glycol, oleic acid, citric acid, fatty acid esters, hydrocarbons etc.

An object of the present invention is to provide film-forming compositions that are thin and transparent so that they form a nearly invisible film on the skin, the film being flexible, fast drying and non-sticky.

Another object of the invention is to provide film-forming compositions that are capable of releasing an active ingredient incorporated therein over a prolonged period of time into the upper layers of the skin so that the composition may be administered less frequently than conventional topical compositions such as creams, ointments or gels.

Another object of the invention is to provide a film-forming composition with improved penetration of the active ingredient incorporated therein into the upper layers of the skin, especially the stratum corneum, in the absence of conventional penetration enhancers such as alcohols or propylene glycol which are potential skin irritants. The stratum corneum may in this case function as a reservoir from which the active ingredient is gradually released.

A further object of the invention is to provide a composition in which the active ingredient will not be significantly degraded, but remains chemically and physically stable throughout the shelf-life of the composition.

SUMMARY OF THE INVENTION

Film-forming compositions disclosed in the literature suffer from the drawback that only a minor proportion of the active ingredient incorporated therein is released from the composition. In the research leading to the present invention, we have surprisingly found that if an oily component is added to the film-forming composition, it is possible to obtain increased release over time of the active ingredient from the resulting film. Thus, it may be possible to obtain extended release of the active ingredient over a period of several days and consequently omit daily applications of a topical composition, which is currently the norm. Furthermore, it may be possible to provide sufficient penetration of the active ingredient into the skin without including a conventional penetration enhancer in the composition.

Accordingly, in one aspect the present invention relates to a sprayable film-forming pharmaceutical composition for dermal application, the composition comprising at least one therapeutically active ingredient dissolved in a pharmaceutically acceptable propellant selected from the group consisting of dimethyl ether, diethyl ether and methylethyl ether, and a mixture of dimethyl ether, diethyl ether and methylethylether and a second propellant selected from $C_{3-5}$ alkanes, hydrofluoroalkanes, hydrochloroalkanes, fluoroalkanes and chlorofluoroalkanes, the propellant being present in an amount of 50-99.5% w/w of the composition, the composition further comprising a film-forming polymer in an amount of 0.1-50% w/w, a plasticizer in an amount of 0.1-10% w/w, and an oily release-enhancing agent in an amount of 0.1-15% w/w.

Film-forming compositions of the invention have been found to form thin, transparent films when applied on skin. The compositions are virtually invisible and therefore more cosmetically acceptable to patients compared to visible patches. The film-forming compositions dry quickly and are not sticky, thus avoiding adhesion to the patients' clothing. When tested for substantivity, i.e. the ability to resist abrasion as a result of washing or general wear after application on skin, compositions including a hydrophobic film-forming polymer tend to exhibit increased substantivity on skin relative to compositions containing a hydrophilic film-forming polymer. Furthermore, the oily release-enhancing agent may act as an emollient to improve hydration of the skin and control transepidermal water loss, thus reinforcing the occlusive effect of the film-forming polymer.

In another aspect, the invention relates to a composition as disclosed herein for use in the treatment of dermal diseases and conditions.

The compositions according to the invention may be dispensed from aerosol containers, typically of the type comprising a container body and valve assembly. The container body may, for instance, comprise a metal body, preferably lined with an chemically inert coating material to avoid degradation of the composition due to interaction between the body and the composition.

The valve assembly may comprise a valve cup, sometimes referred to as a mounting cup, a valve body or housing provided with a valve stem, a spring, a dip tube and an actuator. An inner gasket typically seals a hole in the valve stem, but when the actuator is operated the valve stem is shifted so that the hole is uncovered. Once exposed, the pressure exerted by the propellant in the container body forces the composition to flow through the hole into the dip tube and the valve stem and out through the actuator. As will be understood, when the actuator is released the valve spring returns the valve stem to the position where the hole is once again sealed.

The valve stem and actuator each contain one or more holes (orifices) and channels, the number, size and shape of which are determined in conjunction with the physical properties of the particular composition formulation so as to control both the flow rate through the valve and the characteristics of the spray that emerges from the actuator.

The spray pattern and flow rate may be controlled by means of a separate insert fitted into the outlet orifice of the actuator and which provides the terminal orifice for the actuator assembly. The channel through the insert leading to the outlet typically includes a portion narrower in diameter than the channel in the body of the actuator so that fluid emerging from the actuator channel into the insert channel is caused to swirl and break up into droplets. The insert may be profiled, for example it may be stepped, so that the composition is forced forwards and out of the terminal orifice in a forward motion, rather than the more usual rotational motion. This results in a homogeneous or solid spray pattern and hence enabling a user better to focus the composition on the area of skin being treated.

Since inhalation of the composition according to the invention is not desirable, it is preferred that the dimensions of the fluid channels, orifices, inserts, etc are selected to avoid production of a fine mist on expulsion.

The valve assembly may comprise a metering valve to permit only a metered quantity of the composition to be dispensed with each actuation of the actuator.

For storage, safety and/or hygiene reasons, the actuator may be provided with an protective hood or overcap, separate or integral therewith. The overcap may be moveable from a first position in which the terminal orifice is enclosed to a second position where the orifice is exposed; in the second position, the cover may also function as a directing nozzle by limiting the spray area. The actuator itself may comprise a simple button actuator, or may for example comprise a flip-top or twist-lock. In another arrangement, an overcap having an integral finger actuator may be secured to the container and cover an underlying actuator button. The underside of the overcap may include for example a plurality of projections for contacting the actuator button upon movement due to finger pressure of the operator and triggering the valve to open.

Alternatively, or in addition thereto, the actuator may be moveable between a first position in which the valve is prevented from being intentionally or accidentally operated and a second operative position. For example, part of the valve assembly may be rotatable about the valve stem such that in one rotary position the actuator is operable to dispense the product while in another rotary position the actuator aligns with projections or abutments on the container to prevent actuation. Such a "twist and spray" mechanism may include tactile or audible indications of the open and closed positions.

The inclusion of a tamper-evidence tab, which has to be broken before first use of the aerosol container, is desirable.

BRIEF DESCRIPTION OF THE DRAWINGS

FIG. 7 shows a cross-section of a valve assembly to be mounted on the body of a container body (1), comprising a valve cup (3) provided with sealing (31) between the container body (1) and the valve cup (3) and a gasket (32), a valve body (5) provided with a valve stem (51) and a spring (53) connected to an actuator (4) provided with an insert (44) with a terminal orifice (41) through which the composition present in the container body (1) is expelled when the actuator (4) is depressed. The valve stem (51) contains an aperture (52) through which the composition present in the container body (1) may flow when the actuator is depressed. The valve body is further provided with a tailpiece (55) to which the dip tube (2) is connected. The tailpiece (55) is provided with an aperture (54) permitting the composition to flow from the dip tube (2).

DETAILED DISCLOSURE OF THE INVENTION

Definitions

The term "vitamin D derivative" is intended to indicate a biologically active metabolite of vitamin $D_3$, such as calcitriol, or a precursor to such a metabolite, such as alfacalcidol.

The term "vitamin D analogue" is intended to indicate a synthetic compound comprising a vitamin D scaffold with sidechain modifications and/or modifications of the scaffold itself. The analogue exhibits a biological activity on the vitamin D receptor comparable to that of naturally occurring vitamin D compounds.

"Calcipotriol" is a vitamin D analogue of the formula

Calcipotriol has been found to exist in two crystalline forms, an anhydrate and a monohydrate. Calcipotriol monohydrate and its preparation are disclosed in WO 94/15912.

The term "storage stability" or "storage stable" is intended to indicate that the composition exhibits chemical and physical stability characteristics that permit storage of the composition for a sufficient period of time at refrigeration or, preferably, room temperature to make the composition commercially viable, such as at least 12 months, in particular at least 18 months, and preferably at least 2 years.

The term "chemical stability" or "chemically stable" is intended to mean that no more than 10%, preferably no more than 6%, of the active ingredients degrades over the shelf-life of the product, typically 2 years, at room temperature. An approximation of chemical stability at room temperature is obtained by subjecting the composition to accelerated stability studies at 40° C. where the composition is placed in a heating cupboard at 40° C. and samples are taken at 1, 2 and 3 months and tested for the presence of degradation products by HPLC. If less than about 10% of the substance has degraded after 3 months at 40° C., this is usually taken to correspond to a shelf-life of 2 years at room temperature. When the active ingredient included in the composition is calcipotriol, "chemical stability" usually indicates that the calcipotriol does not degrade significantly over time to 24-epi calcipotriol or other degradation products of calcipotriol in the finished pharmaceutical product.

The term "physical stability" or "physically stable" is intended to mean that the active ingredients do not precipitate from the propellant or vehicle phases throughout the shelf life of the composition.

The term "substantially anhydrous" is intended to mean that the content of free water in the ointment composition does not exceed about 2% by weight, preferably not about 1% by weight, of the composition.

The term "medium-chain triglycerides" is used to indicate triglyceride esters of fatty acids with a chain length of 6-12 carbon atoms. A currently favoured example of such medium chain triglycerides is a mixture of caprylic ($C_8$) and capric ($C_{10}$) triglycerides, e.g. available under the trade name Miglyol 812.

The term "skin penetration" is intended to mean the diffusion of the active ingredient into the different layers of the skin, i.e. the stratum corneum, epidermis and dermis.

The term "skin permeation" is intended to mean the flux of the active ingredient through the skin into the systemic circulation or the receptor fluid of the Franz cell apparatus used in the experiment.

The term "release" is intended to indicate the amount of active ingredient leaving the composition when it is applied on a surface, e.g. a silicone membrane. The in vitro release through the membrane may be determined by the method disclosed in Example 2. In this context, the term "extended release" is intended to mean that the release of the active ingredient takes place over a period of at least 48 hours, such as 72 hours. The term "increased release" is intended to indicate that the total amount of active ingredient released over time is increased from a film-forming composition containing both a plasticizer and an oily release-enhancing agent compared to a film-forming composition containing the film-forming polymer alone or together with a plasticizer, but not an oily release-enhancing agent.

The term "low-molecular volatile solvent" is used to indicate a lower alcohol such as methanol, ethanol, isopropanol or butanol, a $C_{1-4}$ ester of a $C_{1-4}$ carboxylic acid such as methyl acetate, ethyl acetate, butyl acetate, methyl formate or propyl propionate, or acetone.

Embodiments

In the present composition, the film-forming polymer may be selected from the group consisting of cellulose derivatives, acrylic polymers, acrylic copolymers, methacrylate polymers, methacrylate copolymers, polyurethanes, polyvinylalcohol or a derivative thereof such as polyvinylacetate, silicone polymers and silicone copolymers, or copolymers thereof.

When the film-forming polymer is a cellulose derivative, it may be selected from the group consisting of ethyl cellulose, methyl cellulose, hydroxyethyl cellulose, hydroxypropyl cellulose, hydroxypropylmethyl cellulose.

When the film-forming polymer is an acrylic polymer, it may be selected from the group consisting of methyl methacrylate and butyl methacrylate copolymer, ethyl acrylate and methyl methacrylate copolymer, acrylate and ammonium methacrylate copolymer type A and type B, and acrylates/octylacrylamide copolymer.

In the present composition, the plasticizer may be selected from the group consisting of triethyl citrate, tributyl citrate, acetyl triethyl citrate, triacetin, dibutyl sebacate and polyethylene glycol 100-1000, such as polyethylene glycol 400.

Incorporation of a plasticizer in the film-forming composition decreases the glass transition temperature (Tg) of the film-forming polymer. Tg is an indirect indicator of film flexibility as the polymeric film is flexible at temperatures below Tg. Thus, Tg values below skin temperature indicates that the film is flexible on skin. In a specific embodiment, a decreased Tg has been obtained for film-forming compositions containing an acrylic polymer as the film-forming polymer and triethyl citrate as the plasticizer.

The oily release-enhancing agent may be selected from the group consisting of
(a) a polyoxypropylene fatty alkyl ether;
(b) an isopropyl ester of a straight or branched chain $C_{10-18}$ alkanoic or alkenoic acid;
(c) a propylene glycol mono- or diester of a $C_{8-14}$ fatty acid;
(d) a straight or branched $C_{8-24}$ alkanol or alkenol;
(e) a $C_{6-22}$ acylglyceride;
(f) N-alkylpyrrolidone or N-alkylpiperidone; and
(g) a mineral oil such as liquid paraffin.

When the oily release-enhancing agent is a polyoxypropylene fatty alkyl ether, it may be selected from the group consisting of polyoxypropylene-15-stearyl ether, polyoxypropylene-11-stearyl ether, polyoxypropylene-14-butyl ether, polyoxypropylene-10-cetyl ether or polyoxypropylene-3-myristyl ether.

When the oily release-enhancing agent is an isopropyl ester of a straight or branched chain $C_{10-18}$ alkanoic or alkenoic acid, it may be selected from the group consisting of isopropyl myristate, isopropyl palmitate, isopropyl isostearate, isopropyl linolate or isopropyl monooleate.

When the oily release-enhancing agent is a propylene glycol monoester of a $C_{8-14}$ fatty acid, it may be propylene glycol monolaurate or propylene glycol monocaprylate, and when it is a propylene glycol diester of a $C_{8-14}$ alkanoic acid, it may be propylene glycol dipelargonate.

When the oily release-enhancing agent is a straight $C_{8-24}$ alkanol, it may be capryl, lauryl, cetyl, stearyl, oleyl, linoelyl or myristyl alcohol, or when it is a branched $C_{8-24}$ alkanol it may be a branched $C_{18-24}$ alkanol such as 2-octyldodecanol.

When the oily release-enhancing agent is a $C_{6-22}$ acylglyceride, it may be a vegetable oil, e.g. sesame oil, sunflower oil, palm kernel oil, corn oil, safflower oil, olive oil, avocado oil, jojoba oil, grape kernel oil, canola oil, wheat germ oil, almond oil, cottonseed oil, peanut oil, walnut oil or soybean oil, a highly purified vegetable oil, e.g. medium chain triglycerides (caprylic/capric triglycerides), long chain triglycerides, castor oil, caprylic monoglyceride, caprylic/capric mono- and diglycerides or caprylic/capric mono-, di- and triglycerides.

It has been found that using a pure $C_{3-5}$ alkane such as butane as the propellant may not lead to sufficient dissolution of the active ingredient so that the active ingredient may precipitate out of the solution with time and result in crystal growth such that the composition is not physically stable for the entire shelf-life. Further, it has been found that this problem is minimized when dimethyl ether is used as the propellant on its own or even when a proportion of dimethyl ether is added to the $C_{3-5}$ alkane to form a propellant mixture. Thus, in a currently preferred embodiment the present composition comprises dimethyl ether as the sole propellant or in admixture with a $C_{3-5}$ alkane as the second propellant.

In the present composition, the $C_{3-5}$ alkane is preferably selected from the group consisting of n-propane, isopropane, n-butane or isobutane. A particularly favoured $C_{3-5}$ alkane is n-butane and/or isobutane.

In the propellant mixture, the ratio of n-butane and/or isobutane to dimethyl ether may favourably be in the range of 6:1-0:1 v/v, such as 5:1-1:2, 4:1-1:1, 4:2-1:1, 4:2-4:3 or 4:3-1:1.

The present composition may if needed comprise a co-solvent which is a low-molecular volatile solvent. It is, however, currently preferred that the present composition is essentially free from a low-molecular volatile solvent due to the potentially irritative effect of such solvents when applied on skin.

The present composition may comprise a small amount of water which acts as a further plasticizer or as a co-solvent. It is, however, currently preferred that the composition is substantially anhydrous.

To reduce or delay crystallisation of the active ingredient in the applied, dry film-forming composition, it may be an advantage to include an anti-nucleating agent. The anti-nucleating agent may suitably be selected from polymers such as polyvinyl alcohol, hydroxypropyl cellulose, hydroxypropylmethyl cellulose, methyl cellulose and carboxymethyl cellulose.

The active ingredient included in the present film-forming composition may suitably be selected from the group consisting of vitamin D derivatives or analogues, corticosteroids, phosphodiesterase 4 inhibitors, ingenol derivatives, retinoids such as adapalene, JAK inhibitors, NK-1 receptor antagonists, antibiotics such as fusidic acid or clindamycin, calcineurin inhibitors such as tacrolimus or pimecrolimus, keratolytic agents such as salicylic acid or lactic acid, non-steroidal anti-inflammatory agents and local anesthetics such as lidocain.

The vitamin D derivative or analogue may be selected from calcipotriol, calcitriol, tacalcitol, maxacalcitol, paricalcitol and alfacalcidol. A preferred vitamin D analogue which has been shown to be effective in the treatment of psoriasis is calcipotriol. Before dissolution in the propellant or co-solvent, calcipotriol may be in the form of anhydrate or monohydrate, preferably the monohydrate.

The corticosteroid may be selected from the group consisting of amcinonide, betamethasone, budenoside, clobetasol, clobetasone, cortisone, desonide, desoxycortisone, desoximethasone, dexamethasone, diflucortolon, diflorasone, flucortisone, flumethasone, flunisolide, fluocinonide, fluocinolon, fluorometholone, fluprednisolone, flurandrenolide, fluticasone, halcinonide, halobetasol, hydrocortisone, mepredinsone, methylprednisone, mometasone, paramethasone, prednicarbate, prednisone, prednisolone and triamcinolone or a pharmaceutically acceptable ester or acetonide thereof. The corticosteroid may preferably be selected from betamethasone, budenoside, clobetasol, clobetasone, desoximethasone, diflucortolon, diflorasone, fluocinonide, fluocinolon, halcinonide, halobetasol, hydrocortisone, mometasone and triamcinolone or a pharmaceutically acceptable ester thereof. The corticosteroid ester may for instance be betamethasone acetate, betamethasone dipropionate, betamethasone valerate, clobetasol propionate, dexamethasone acetate, flumethasone pivalate, fluticasone propionate, hydrocortisone acetate, hydrocortisone butyrate or mometasone furoate. The acetonide may be selected from fluocinolone acetonide or triamcinolone acetonide. The corticosteroid is preferably betamethasone dipropionate or betamethasone valerate.

In a currently favoured embodiment, the composition comprises calcipotriol or calcipotriol monohydrate as the vitamin D analogue and betamethasone valerate or betamethasone dipropionate as the corticosteroid.

The phosphodiesterase 4 inhibitor may for instance be selected from the compounds disclosed in WO 2008/077404, WO 2008/104175, WO 2008/128538 or WO 2010/069322 the disclosure of which is included herein by reference. A particularly preferred phosphodiesterase 4 inhibitor is 2-{6-[2-[2,3-dichloropyridin-4-yl)acetyl]-2,3-dimethoxyphenoxy}-N-propylacetamide.

The ingenol derivative may suitably be selected from the group consisting of ingenol-3-angelate, ingenol-5-angelate, ingenol-20-angelate, 20-O-acetyl-ingenol-3-angelate and 20-deoxy-ingenol-3-angelate. Ingenol-3-angelate, also known as ingenol-3-mebutate or PEP 005, has recently been approved in the US and EU for the treatment of actinic keratosis.

In a specific embodiment, the film-forming composition of the invention comprises a therapeutically active ingredient and

| | |
|---|---|
| Acrylates/ammonium methacrylate copolymer | 0.5-1.0% w/w |
| Medium chain triglycerides | 0.1-0.5% w/w |
| Tributyl citrate | 0.1-0.3% w/w |
| Butane | 50-60% w/w |
| Dimethyl ether | 40-50% w/w |

The present composition may also comprise other components commonly used in dermal formulations, e.g. antioxidants (e.g. alpha-tocopherol), preservatives, pigments, emollients, skin soothing agents, skin healing agents and skin conditioning agents such as urea, glycerol, allantoin or bisabolol, cf. *CTFA Cosmetic Ingredients Handbook*, $2^{nd}$ Ed., 1992. In a favoured embodiment, the composition may comprise an anti-irritative agent such as menthol, eucalyptol or nicotinamide.

The composition of the invention may be used in the treatment of psoriasis, sebopsoriasis, pustulosis palmoplantaris, atopic dermatitis, contact dermatitis, eczema, actinic keratosis, pruritus, ichtyosis, rosacea and acne and related skin diseases by topically administering an effective amount of a composition according to the invention to a patient in need of such treatment. Said method preferably comprises topical administration once or twice a day of a therapeutically sufficient dosage of said composition. To that end, the composition according to the invention preferably contains about 0.0001-1% w/w of the active ingredient. It is envisaged that the present composition may advantageously be used for maintenance treatment of these dermal diseases, i.e. continued treatment after the disappearance of visible symptoms of the disease in order to delay recurrence of the symptoms. The present composition has the added advantage for the treatment of skin diseases involving dry or flaky skin, e.g. psoriasis, that the oily release-enhancing agent acts as an emollient hydrating and softening the flaky skin to give the skin a less dry appearance.

In a further aspect, the invention relates to a pressurized container adapted to dispensing a topical composition on an affected skin area, the container comprising a composition according to the invention and a valve assembly and actuator for releasing the composition in the form of a spray.

Figure 6A:
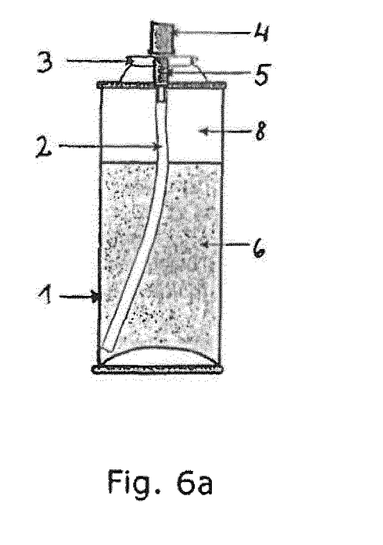
FIG. 6a shows a cross-section of a container intended for a pressurized spray composition of the invention, comprising a container body (1) onto which is fitted a valve assembly comprising a valve cup (3), a valve body (5), an actuator (4) and a dip tube (2). As shown in this embodiment, the present composition may be a two-phase system comprising a composition phase (6) and a vapor phase (8).
Figure 6B:
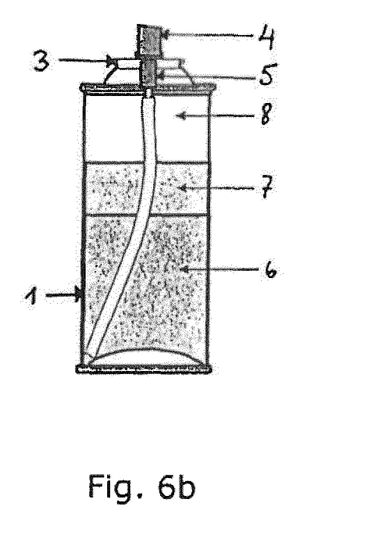
FIG. 6b shows a cross-section of a container intended for a pressurized spray composition of the invention, comprising a container body (1) onto which is fitted a valve assembly comprising a valve cup (3), a valve body (5), an actuator (4) and a dip tube (2). As shown in this embodiment, the present composition may be a three-phase system comprising a vehicle phase (6), a propellant phase (7) and a vapor phase (8).

As shown in FIGS. 6a and 6b, an example of a container suitable for a pressurized product may be composed of a container body (1) in which the present composition is stored, a dip tube (2), and a valve assembly comprising a valve cup (3), a valve body (5) and an actuator (4).

Typically, the container body (1) may be constructed from materials such as metal, glass, ceramics, polyester, polyethylene terephthalate (PET) or other polymer, or the like. Glass containers may be provided with a safety coating of for instance polypropylene to contain glass shards that may be formed on impact with a hard surface. Metal container bodies are currently preferred as they are better able to withstand impact and are amenable to surface coating. Stainless steel, tinplate and aluminium (i.e. aluminium or aluminium alloy, including anodised aluminium) container bodies are especially suitable materials for this purpose, with aluminium being currently preferred as it is light and not readily breakable.

Metal containers are typically lined or coated with an inert material to protect the composition from reactions with the metal, thereby preventing or substantially eliminating any degradation of the active ingredients or other components of the composition.

Inert materials include any suitable polymer, lacquer, resin or other coating treatment that creates a barrier between the container and the composition for preventing any chemical interaction between the composition and the container. Preferably the inert material is a non-metallic coating.

Known coatings for metal containers include acrylic, phenolic, polyester, epoxy and vinyl resins. However, a composition containing a vitamin D derivative or analogue, is likely to be chemically degraded under acidic conditions or in the presence of acidic reacting compounds. Moreover, corticosteroids are known to be chemically degraded under alkaline conditions or in the presence of alkaline reacting compounds. Accordingly, the container coating for use with a composition of the present invention should preferably be selected so that it exhibits no acidic or alkaline reactivity in itself, and that no acidic or alkaline reacting impurities are leached from it in the presence of the composition.

It has been found, for example, that a particular epoxyphenol resin inner lacquer was incompatible with one of the active ingredients, causing unacceptable chemical degradation of calcipotriol. Such degradation may possibly be due to the presence in the lacquer of colophonium which includes an acid group. On the other hand, the chemical stability of calcipotriol was satisfactory when a polyimide-polyamide resin was used as the inner coating.

In addition to polyimide-polyamide coatings, other materials suitable for lining the interior of the metal containers include polyamides, polyimides, polypropylene, polyethylene, fluoropolymers, including perfluoroethylenepropylene copolymer (FEP), fluororubber (FPM), ethylene-propylene diene monomer rubber (EPDM), polytetrafluoroethylene (PTFE), ethylene tetrafluoroethylene copolymer (EFTE), perfluoroalkoxyalkanes, perfluoroalkoxyalkylenes, or blends of fluoropolymers with non-fluorocarbon polymers. Fluoropolymers may, for example, be used in combination with polyimide-polyamide resins.

The container coating material may be applied as a single layer, or in multiple layers, for example allowing each layer to cure before application of a further layer. As well as shielding the composition from the metal container, the application of more than one coating may also help prevent adhesion of the active ingredients on the container walls.

For the same reasons, valve components of the container that are brought into contact with the composition are also preferably made of, or coated with, materials that do not cause degradation of the composition. For example, metal valve components such as the valve cup may be coated with anodized silver, epoxymelamine or polypropylene.

As well as inhibiting leakage from the container, especially leakage of propellant, materials used for gaskets or seals within the container should also preferably be chemically inert. For example, the container body and valve cup may be crimped together using an intermediate gasket which at least in part is exposed to contact with the composition, thus if the gasket is not made of inert material it may over time result in degradation of the composition.

Extensive testing of materials used for gaskets in conventional aerosol container valves has established that polymeric materials prepared by vulcanization using sulphur-containing accelerators (e.g. thiazoles) are not suitable as gasket materials for containers intended to include the present composition, probably due to reactivity of sulphur-containing residues or impurities with one or both of the active ingredients resulting in chemical degradation.

Similarly, gasket materials permeable to the propellants included in the present composition are not suitable as gasket materials for the present purpose.

Suitable gasket or seal materials for use with compositions according the invention include fluoroelastomers (e.g. Viton V 600), fluorinated ethylene-propylene copolymer (FEP), fluororubber (FPM, e.g. VI500) or ethylene-propylene diene monomer rubber (EPDM).

Suitable materials for the dip tube have been found to be e.g. polyethylene and polypropylene. Suitable materials for the valve stem have been found to be e.g. polyamide and acetal (POM).

In the embodiment shown in FIG. 6b, the composition comprises a vehicle phase (6), a propellant phase (7) and a vapor phase (8). In this embodiment the spray container should be shaken thoroughly before use so that the vehicle phase (6) will be homogenously suspended in the propellant phase (7).

Figure 7:
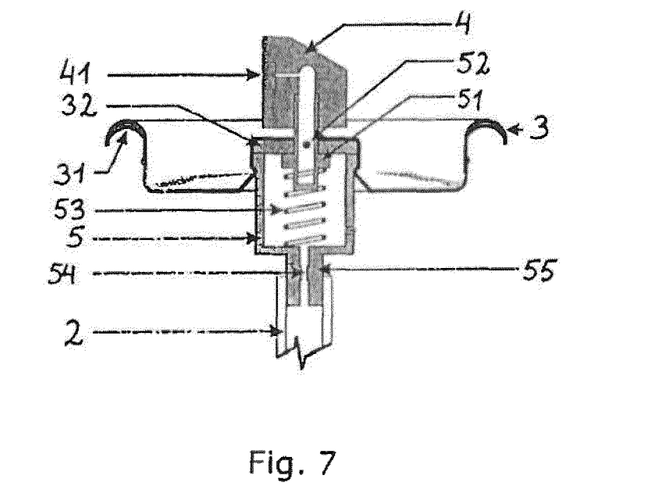

As shown in FIG. 7, the valve assembly may be composed of a valve cup (3), which is typically made of metal such as aluminium, attached to the container body (1) by crimping, a valve body (5) which contains a valve stem (51) and a spring (53) connected to the actuator (4) which is depressed for activation to expel the composition from the container. The valve stem (51) contains at least one aperture (52) with a diameter of 0.05-1 mm through which the composition present in the container may flow when the actuator (4) is depressed. The valve stem aperture (52) may preferably be provided with a ball which allows the container to be used in different positions such as upside down or sideways.

The actuator (4) is provided with an insert (44) having a terminal orifice (41) with a diameter of 0.3-1.5 mm through which the composition is expelled. The actuator (4) should be designed so as to provide an aerosol spray from the orifice (41) with droplets of a size sufficiently small to ensure a uniform spray of the product, yet sufficiently large to ensure that the droplets of composition do not form a fine mist on expulsion from the container such that droplets containing biologically active substances may be accidentally inhaled.

The dimensions of the insert orifice (41) and valve stem aperture(s) (52) as well as the pressure within the container generally determine the width of the spray cone formed when the composition is expelled from the aperture (4) and consequently the size of the area that will be covered by the sprayed composition.

In a particular embodiment, the container may be provided with means for metering a dose of the composition.

The invention is further illustrated by the following examples which are not in any way intended to limit the scope of the invention as claimed.

EXAMPLES

Example 1

Compositions

Reference compositions were prepared including the following ingredients.

| | Plasticizer | | | | Oil | Solvent |
|---|---|---|---|---|---|---|
| Polymer | TEC | TBC | DBS | PEG | MCT | Ethanol |
| Klucel LF 5% | X | X | X | X | X | X |
| Eudragit E 15% | X | | | | | X |
| Eudragit RS 15% | X | X | X | X | | X |
| Dermacryl 79 10% | X | | | | X | X |
| Dermacryl 79 + Klucel LF | | | | | X | X |

TEC: triethyl citrate
TBC: tributyl citrate
DBS: dibutyl sebacate
PEG: polyehtylene glycol 400
MCT: medium chain triglycerides The content of plasticizer and/or oil in the compositions was 20% by weight of the dry film-forming polymer. In addition, 1.2% by weight of betamethasone valerate (1% by weight betamethasone) was added to the compositions.

To prepare the vehicle, the plasticizer/oil was dissolved in the solvent by stirring for 1-2 hours. The film-forming polymer was added slowly with stirring, and the resulting mixture was stirred overnight to complete the dissolution of the polymer.

Example 2

Compositions

| Ingredients (mg/g) | 01 | 02 | 03 | 04 | 05 | 06 |
|---|---|---|---|---|---|---|
| Eudragit RS PO | 7.8 | 7.8 | 7.8 | 7.8 | 7.8 | 7.8 |
| Tributyl citrate | | 1.6 | 0.0 | 1.6 | 1.6 | 0.0 |
| Medium chain triglycerides | | | 1.6 | 1.6 | 3.1 | 3.1 |
| BDP | 1.6 | 1.6 | 1.6 | 1.6 | 1.6 | 1.6 |
| Butane | 531.8 | 531.0 | 531.0 | 530.2 | 529.3 | 530.2 |
| Dimethyl ether | 458.8 | 458.1 | 458.1 | 457.4 | 456.7 | 457.4 |

To prepare a sprayable film-forming composition, the active ingredient, plasticizer, oil and optionally other excipients were weighed into spray containers that were closed by inserting valve and crimping. Dimethyl ether and butane was added through the valve, and the containers were shaken to dissolve the ingredients in the propellant mixture.

Example 3

In Vitro Release Testing of Compositions of Example 1

The purpose of the study is to explore the effect of polymer and plasticizer or oily release-enhancing agent on the in vitro release of Betamethasone-17-valerate (BMV) from compositions according to Example 1, with a view to optimising the type and concentration of polymer and plasticizer with regard to obtaining a prolonged release profile. This is done by testing various types and concentrations of polymers and plasticizers, as these are parameters expected to affect drug release from the polymeric in situ forming films.

Membrane:
Dow Corning® 7-4107 Silicone Elastomer Membrane, 75 µm.

Diffusion Cell System:
Modified dialysis cells (LEO Pharma, Denmark).
Receptor compartment: ~1.5 ml. The actual volume of each cell is registered by weighing of the assembled cell before and after filling of the receptor compartment. Diameter: ~1.55 cm, corresponding to an available diffusion area of 1.89 $cm^2$.

Sheets of silicone membrane are cut to size (circles, Ø=22 mm). The membrane is placed between the two compartments of the dialysis cells with the glossy side facing the donor compartment.

The receptor compartment is filled with preheated receptor medium (the actual volume of each cell is registered by weighing) and possible air bubbles removed. The sampling arm is sealed with a plastic bung and/or parafilm to prevent evaporation of the receptor medium. Uniform mixing of the receptor phase is obtained with a magnetic bar placed in the receptor compartment. The diffusion cells are placed in a heating cabinet set at ~37° C. to maintain a temperature of ~32° C. at the membrane surface. The stirring bed is set at 300 rpm. The cells are allowed to equilibrate for minimum 30 min before application of FFS and thus start of experiment.

Receptor Medium:
10% w/w methyl-β-cyclodextrin in 0.1M acetate buffer pH 4.5. The receptor medium is degassed in an ultrasound water bath for 20 minutes prior to the start of the experiment and before 24 h and 48 h sampling. It was ensured that sink conditions were present at all times during the study period; i.e. that the concentration of the drug compounds in the recipient phase was below 10% of the solubility of the drug substances in the medium.

Application, Occlusion, Dosage and Volume of Test Formulation:

240 µl film-forming composition (FFC) is gently applied and distributed on the membrane surface (t=0 h) using an eppendorf pipette. The pipette is not tared before application as previous experiments showed no significant retention of formulation. This may partly be a consequence of solvent evaporation complicating the registration of possible formulation retention. The weight of 240 µl FFC is registered to be used in the data processing of the release results The volume of FFC delivered by an eppendorf pipette may vary as a consequence of the varying viscosity of the FFC. Therefore, the weight of 10 consecutive applications of 240 µl FFC (the corresponding placebo formulation is used for this purpose) is registered, an average calculated and used in the data processing of the release results.

After application of FFC the dialysis cell is placed back on the stirring bed. The cell is placed with the membrane horizontally to obtain an even distribution of FFC during solvent evaporation/film formation by hindering of accumulation of the FFC/film in the bottom of the donor compartment.

Exposure and Sampling Times:
Samples of 1500 µl (the actual volume is weighed and registered) are withdrawn from each cell at regular time intervals. After each sampling the receptor compartment is refilled with preheated fresh receptor medium. The withdrawn samples are stored in sealed HPLC vials at 2-8° C. and protected from light until quantification by HPLC analysis. Sampling time points: 0, 1, 6, 24, 30, 48, 54, 72 h.

Study Design:
Each formulation is tested in 3 replicates (n=3).

HPLC Analysis:
HPLC analysis in New Products, Analytical department according to protocol 130-FKFT-20110614A.

Data Analysis:
The analytically determined BMV assay values were correspondingly corrected for the replenishments. The drug concentrations are transferred to a spread sheet (Excel) to calculate the cumulative amount released over the period of 0 to 72 h. The release rate is calculated from the linear part of the curve of the cumulative amount released versus square root of time. Based on the data of all individual cells in a group, the mean value and the standard deviation (SD) are calculated for each group.

Figure 1:
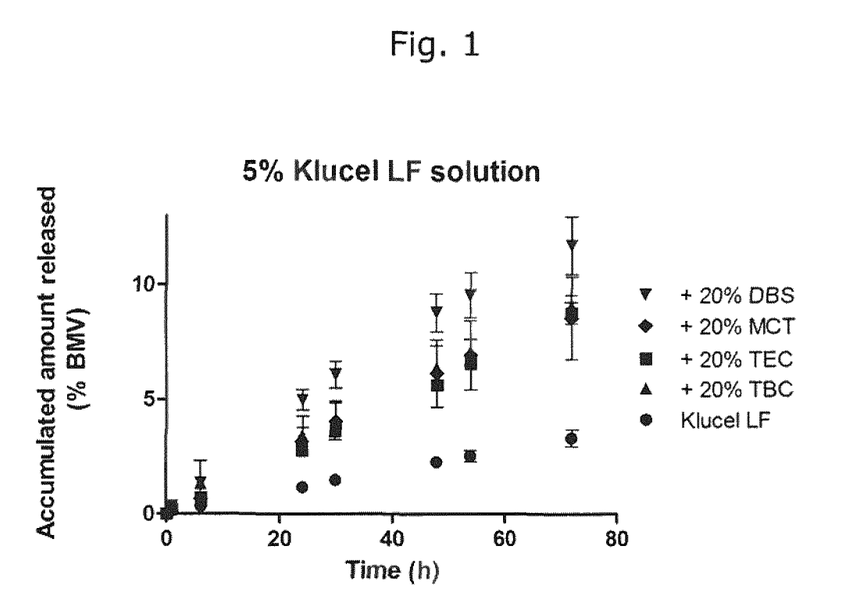
FIG. 1 shows the release of betamethasone valerate (BMV) from a film-forming composition containing Klucel LF and 20% (by weight of the dry film-forming polymer) of the plasticizers TEC, TBC and DBS, or the oily release-enhancing agent MCT compared to the release of BMV from a film-forming composition containing no plasticizer or oily release-enhancing agent over a period of 72 hours.
Figure 2:
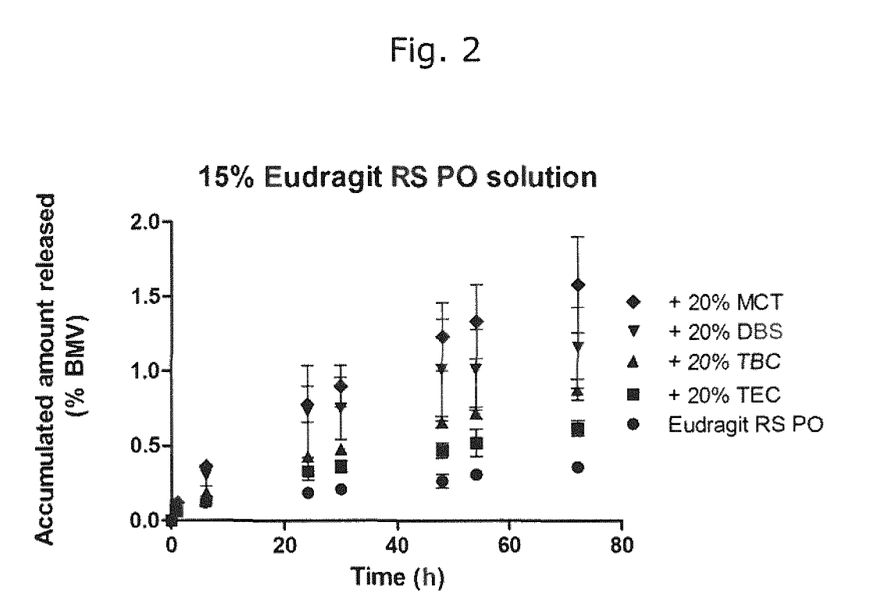
FIG. 2 shows the release of BMV from a film-forming composition containing Eudragit RS PO and 20% (by weight of the dry film-forming polymer) of the plasticizers TEC, TBC and DBS, or the oily release-enhancing agent MCT compared to the release of BMV from a film-forming composition containing no plasticizer or oily release-enhancing agent over a period of 72 hours.

Results
The results appear from FIGS. 1 and 2.
FIG. 1 shows the release of BMV from a film-forming composition containing Klucel LF and 20% (by weight of the dry film-forming polymer) of the plasticizers TEC, TBC and DBS, or the oily release-enhancing agent MCT compared to the release of BMV from a film-forming composition containing no plasticizer or oily release-enhancing agent over a period of 72 hours. It appears from FIG. 1 that the inclusion of a plasticizer or oily release-enhancing agent results in a significant increase in the release of active ingredient from the film.

FIG. 2 shows the release of BMV from a film-forming composition containing Eudragit RS PO and 20% (by weight of the dry film-forming polymer) of the plasticizers TEC, TBC and DBS, or the oily release-enhancing agent MCT compared to the release of BMV from a film-forming composition containing no plasticizer or oily release-enhancing agent over a period of 72 hours. It appears from FIG. 2 that the inclusion of a plasticizer or oily release-enhancing agent results in a significant increase in the release of active ingredient from the film.

Example 4

In vitro Release Testing of Compositions of Example 2

The purpose of the study is to explore the effect of polymer, plasticizer and oily release-enhancing agent on the in vitro release of BDP from compositions according to Example 2, with a view to optimising the concentration of oily release-enhancing agent with regard to obtaining a prolonged release profile.

Membrane:
Dow Corning® 7-4107 Silicone Elastomer Membrane, 75 μm.

Diffusion Cell System:
Modified dialysis cells (LEO Pharma, Denmark).
Receptor compartment: ~3.75 ml. The actual volume of each cell is registered by weighing of the assembled cell before and after filling of the receptor compartment. Diameter: ~1.55 cm, corresponding to an available diffusion area of 1.89 cm$^2$.

Sheets of silicone membrane are cut to size (circles, Ø=22 mm). The membrane is placed between the two compartments of the dialysis cells with the glossy side facing the donor compartment.

The formulation is sprayed directly onto the membrane by pressing the actuator 10 times.

The receptor compartment is filled with preheated and degassed receptor medium (the actual volume of each cell is registered by weighing) and possible air bubbles removed. The sampling arm is sealed with a plastic bung and parafilm to prevent evaporation of the receptor medium. Uniform mixing of the receptor phase is obtained with a magnetic bar placed in the receptor compartment. The diffusion cells are placed in a heating cabinet set at ~37° C. to maintain a temperature of ~32° C. at the membrane surface. The stirring bed is set at 300 rpm.

Receptor Medium:
10% w/w methyl-β-cyclodextrin in 0.05M acetate buffer pH 4.0. The receptor medium is degassed in an ultrasound water bath for minimum 20 minutes prior to the start of the experiment and before 24 h and 48 h sampling. It was ensured that sink conditions were present at all times during the study period; i.e. that the concentration of the drug compounds in the recipient phase was below 10% of the solubility of the drug substances in the medium.

Composition of Acetate Buffer

| Excipient (g/L) | 05P | Function |
| --- | --- | --- |
| Acetic acid, glacial | 2.567 | Buffer |
| Sodium acetate trihydrate | 0.988 | Buffer |
| Methyl-β-cyclodextrin | 100 | Solubilising agent |
| Purified water | Ad 1 L | Solvent |
| NaOH/HCl ad | pH 4.0 | |

Preparation of Acetate Buffer
Mix all the excipients. Adjust the pH with either NaOH or HCl to obtain a pH of 4.0. Store the buffer at 5° C. until use.

Exposure and Sampling Times:
Samples of 1500 μl (the actual volume is weighed and registered) are withdrawn from each cell at regular time intervals. After each sampling the receptor compartment is refilled (the exact same volume as withdrawn) with preheated fresh receptor medium. The withdrawn samples are stored in brown sealed HPLC vials at 2-8° C. and protected from light until quantification by HPLC analysis at the end of the experiment.

Sampling time points: 0, 1, 6, 24, 30, 48, 54, 72 h.

Study Design:
Each formulation is tested in 3 replicates (n=3).

Figure 8:
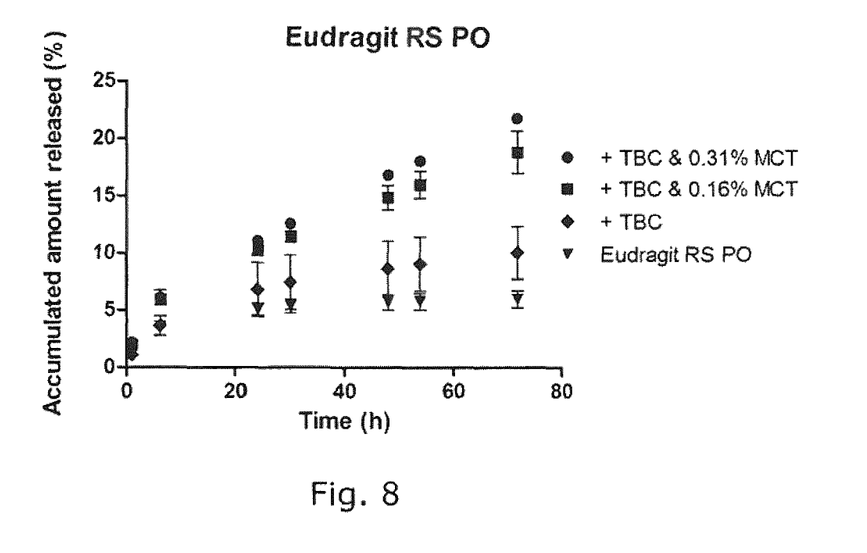
FIG. 8 is a graph showing the accumulated amount of released BDP as a function of time from film-forming compositions containing Eudragit RS PO as the film-forming polymer alone, Eudragit RS PO together with tributyl citrate as the plasticizer or Eudragit RS PO together with tributyl citrate and 0.16% w/w or 0.31% w/w MCT as the oily release-enhancing agent.

Analysis of Samples
Column: Sunfire C18; 3.5 μm or 5 μm; 150×4.6 mm ID or equivalent
Mobile Phase: Acetonitrile/0.01 M (NH$_4$)$_2$HPO$_4$ pH 6.4, 70:30 (v/v).
Flow rate: 0.8 ml/min
Detection Wavelength: 240 nm
Injection volume: 10 μl
Column temperature: 25° C.
Rack temperature: 10° C.
Retention time BDP: ~5.8 min
Runtime: ~8 min Results
The accumulated amount of released BDP (μg/cm$^2$) is shown as a function of time in FIG. 8. The lowest release is observed from the propellant driven spray formulation containing only the film-forming polymer. The addition of tributyl citrate has a release enhancing effect which is further increased by adding 0.16% w/w or 0.31% w/w MCT as the release-enhancing agent.

Example 5

Skin Substantivity Testing
Topical substantivity of compositions according to Example 1 is tested by applying film-forming compositions including a colour additive (curcumin) in an amount of 1 mg/g on excised pig ear skin and determining the ΔE value before and after the film has been washed and dried. The ΔE value is a measure of the difference in skin colour before and after washing and drying. Thus, a substantive film results in a low ΔE value, preferably close to zero.

5% Klucel LF FFS/20% MCT:
ΔE (start→1. Wash/dry)=38
ΔE (start→2. Wash/dry)=42
15% Eudragit RS PO FFS/20% MCT:
ΔE (start→1. Wash/dry)=0.1
ΔE (start→2. Wash/dry)=1.2
10% Dermacryl 79 FFS/20% MCT:
ΔE (start→1. Wash/dry)=0.9
ΔE (start→2. Wash/dry)=1.5
⇨ Klucel<Dermacryl~Eudragit
The difference in substantivity can be ascribed to the water-solubility of the film-forming polymer used in the composition→the hydrophilic Klucel film-forming composition is very easily washed off, i.e. has a very poor substantivity.

Example 6

In vitro Skin Penetration
To investigate the skin penetration and permeation of BMV from compositions according to example 1, a skin diffusion experiment was conducted. Full thickness skin from pig ears was used in the study. The skin was cleaned and kept frozen at −18° C. before use. On the day prior to the experiment the skin was placed in a refrigerator (5±3° C.) for slow defrosting.

Static Franz-type diffusion cells with an available diffusion area of 3.14 cm$^2$ and receptor volumes ranging from 8.6 to 11.1 ml were used in substantially the manner described by T.

J. Franz, "The finite dose technique as a valid in vitro model for the study of percutaneous absorption in man", in *Current Problems in Dermatology*, 1978, J. W. H. Mall (Ed.), Karger, Basel, pp. 58-68. The specific volume was measured and registered for each cell. A magnetic bar was placed in the receptor compartment of each cell. After mounting the skin, physiological saline (35° C.) was filled into each receptor chamber for hydration of the skin. The cells were placed in a thermally controlled water bath which was placed on a magnetic stirrer set at 300 rpm. The circulating water in the water baths was kept at 35±1° C. resulting in a temperature of about 32° C. on the skin surface. After 30 min the saline was replaced by the receptor medium, 15 mM isotonic acetate buffer, pH 5.5, containing 1% methyl-β-cyclodextrin. Sink conditions were maintained at all times during the period of the study, i.e. the concentration of the active compound in the receptor medium was below 10% of the solubility of the compound in the medium.

The in vitro skin permeation of each test composition containing $^3$H-BMV was tested in 6 replicates (i.e. n=6). Each test composition was applied on the skin membrane at 0 hours using a pipette.

The skin penetration experiment was allowed to proceed for 24 hours. Samples were then collected from the following compartments at 2, 6 and 24 h (only the receptor medium was sampled at 24 h):

The remaining film was removed, and the stratum corneum was collected by tape stripping once using up to 15 D-Squame® tape discs (diameter 22 mm, CuDerm Corp., Dallas, Tex., USA). Each tape disc is applied to the test area using a standard pressure for 10 seconds and removed from the test area in one gentle, continuous move. For each repeated strip, the direction of tearing off was varied. The viable epidermis and dermis was then sampled from the skin in a similar fashion.

Samples (1 ml) of the receptor fluid remaining in the diffusion cell were collected and analysed.

The concentration of $^3$H-BMV in the samples were determined by liquid scintillation counting.

Figure 3:
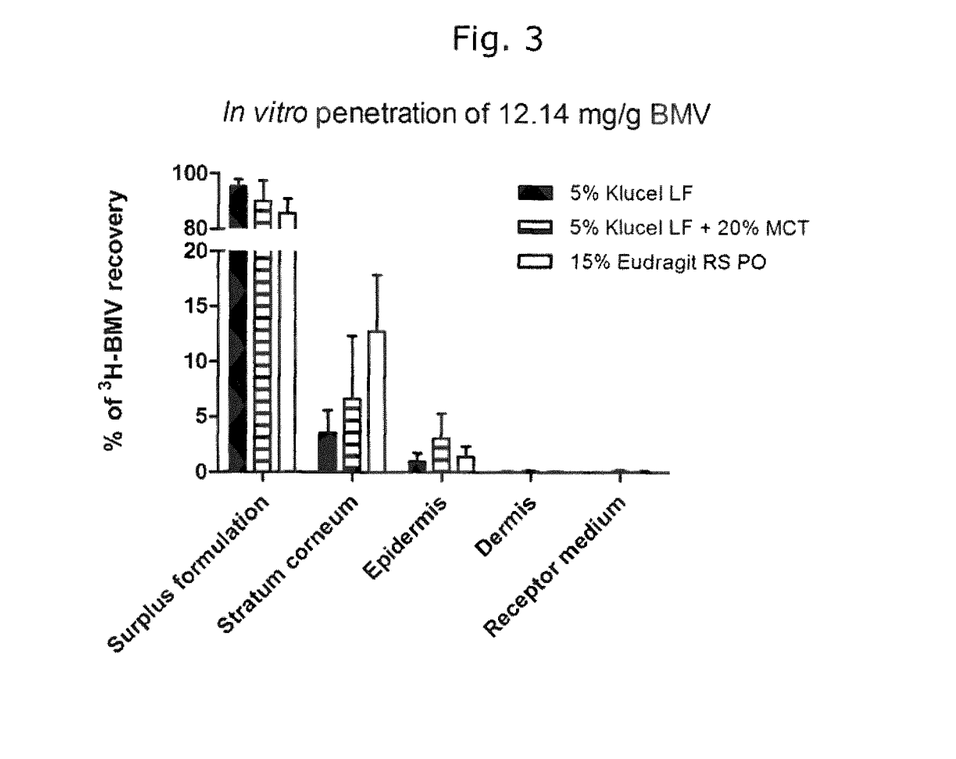
FIG. 3 shows penetration of BMV from all three test compositions in the course of 24 hours.

The results appear from FIG. 3 below showing that in the course of 21 hours BMV penetrated from all three test compositions, and that the BMV mainly accumulated in the stratum corneum rather than in the epidermis. More of the BMV penetrated from the Klucel LF composition containing 20% (by weight of dry film-forming polymer) MCT than from the Klucel LF composition without plasticizer or oily release-enhancing agent. None of the BMV permeated into the receptor medium.

Example 7

In vivo Penetration into the Skin of Hairless Rats

Compositions similar to those described in Example 1, but containing betamethasone dipropionate (BDP; 0.643 mg/g) as the active ingredient and Dermacryl 79 (blue), DynamX (red) and Eudragit RL PO (green) as the film-forming polymers are investigated for penetration into the skin of hairless rats over a period of 7 days. A betamethasone ointment (purple) is used as a comparative formulation.

Male hairless rats of the OFA-hr/hr strain are obtained from Charles River, USA.

The rats are weighed prior to study initiation. Under isofluorane anesthesia, 100 µl of formulation is applied to a 4×3 cm area on the back of each rat. The rat is left for 2 minutes to permit the formulation to dry, and an Optiskin film (5.3×7.2 cm, URGO Laboratories, France) is applied over the area and on top of that, Fixomull stretch (BSN Medical, Germany).

Sublingual blood samples are collected from the animals in each group to be terminated 24 h post dosing. The samples are drawn 30 min, 2 h, 4 h and 6 h post dosing.

Animals are terminated at either 24 h or 7 days post dosing. Sublingual blood samples are collected from each animal prior to termination. The rats are euthanized with $CO_2$. Skin biopsies are taken from the applied skin area. The skin is cleaned gently with a tissue soaked in 99.9% ethanol. The biopsies are weighed and kept at −80° until quantitative analysis.

The concentration of BDP or betamethasone in the samples is determined by LC mass spectrometry.

The results appear from FIGS. 4 and 5 below.

Figure 4:
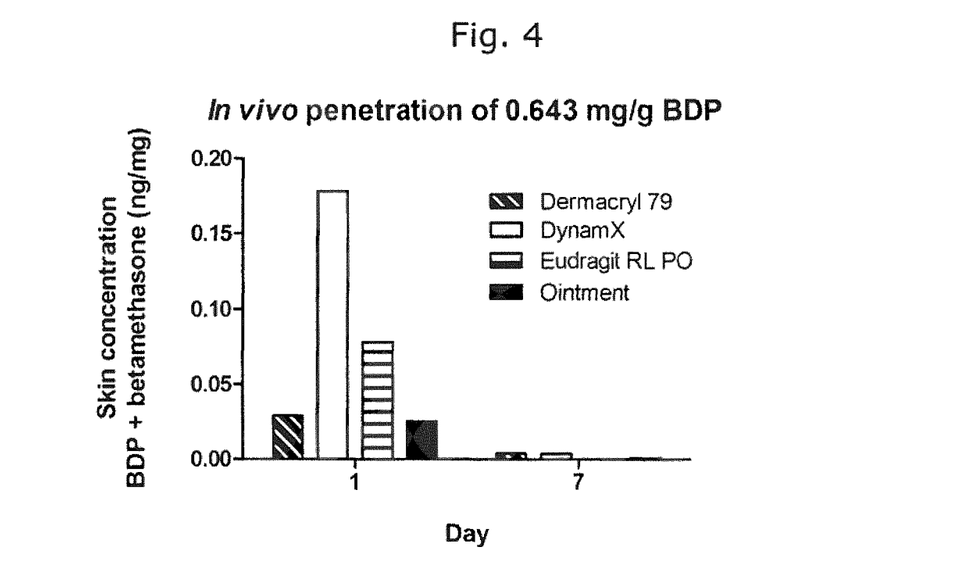
FIG. 4 shows the concentration of betamethasone dipropionate (BDP) and its metabolite betamethasone in the skin of hairless rats after 1 day and 7.

FIG. 4 shows the skin concentration of BDP and its metabolite betamethasone after 1 day and 7 from which it appears that the skin penetration after one day is highest from a film-forming composition containing DynamX as the film-forming polymer, and that application of film-forming compositions containing DynamX or Eudragit RL PO as the film-forming polymer results in higher penetration of the active ingredient that when the comparative ointment is applied. In further appears that BDP and/or betamethasone remains in the skin for 7 days after application of a film-forming composition containing Dermacryl 79 or DynamX.

Figure 5:
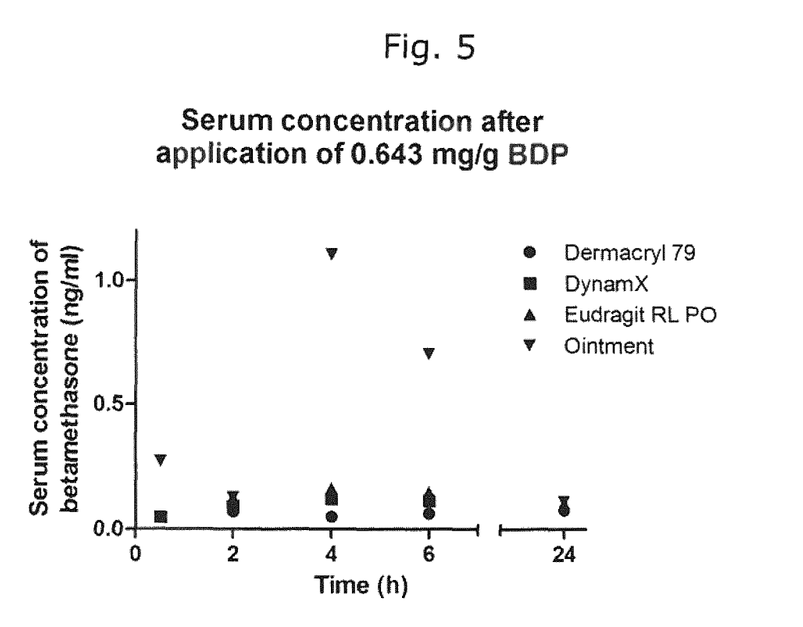
FIG. 5 shows the serum concentration of betamethasone over 24 h from application on the skin of hairless rats of film-forming compositions and the comparative ointment.

FIG. 5 shows the serum concentration of betamethasone over 24 h from application of the film-forming compositions and the comparative ointment. It appears that application of the ointment leads to permeation through the skin, whereas hardly any betamethasone is found in serum after application of the film-forming compositions.

Example 8

In vivo Penetration into the Skin of Hairless Guinea-pigs

The objective of this study is to investigate the pharmacokinetics in skin of betamethasone dipropionate over an extended period of time (7 days) after application of film-forming compositions 1, 2, 4 and 5 of Example 2 on the flank of hairless guinea-pigs.

The study was performed in 12 female IAF hairless guinea-pigs, Crl:HA-Hr$^{hr}$ from Charles River. The animals were housed according to standard routines at LEO Pharma.

Prior to dosing, the animals were anaesthetized with a mixture of ketamine 50 mg/kg and xylazine 5 mg/kg i.p (1.25 ml/kg), The compositions were applied by spraying according to the schedule below, and the dosing area was controlled by spraying through a dosing template of filter paper with a circular hole (18 mm diameter). All formulations were applied by 5 bursts of spray.

| Date | Animal no. | RB Tx field | RF Tx field | LB Tx field | LF Tx field |
| --- | --- | --- | --- | --- | --- |
| 2013-06-13 | 1 | 1 | 2 | 4 | 5 |
| 2013-06-13 | 2 | 5 | 4 | 2 | 1 |
| 2013-06-13 | 3 | 3 | 4 | 1 | 2 |
| 2013-06-17 | 4 | 1 | 2 | 4 | 5 |
| 2013-06-17 | 5 | 5 | 4 | 2 | 1 |
| 2013-06-17 | 6 | 4 | 5 | 1 | 2 |
| 2013-06-19 | 7 | 1 | 2 | 4 | 5 |
| 2013-06-19 | 8 | 5 | 4 | 2 | 1 |
| 2013-06-19 | 9 | 4 | 5 | 1 | 2 |
| 2013-06-20 | 10 | 1 | 2 | 4 | 5 |
| 2013-06-20 | 11 | 5 | 4 | 2 | 1 |
| 2013-06-20 | 12 | 4 | 5 | 1 | 2 |

After application of the compositions, the animals were observed regularly. Parameters observed were:

Local skin reaction at sites of administration, any behavioural signs of discomfort or irritation by the formulations, visible remains of the formulations.

The animals treated on Thursday 2013-06-20 were terminated 2 hours after treatment.

Each animal was anaesthetized with a mixture of ketamine 50 mg/kg and xylazine 5 mg/kg i.p (1.25 ml/kg), and the animals were euthanized by asphyxiation in $CO_2$. Each test site was gently swabbed twice with soaked cotton in order to remove any excess formulation, and one 4 mm punch biopsy was taken from each site. Subsequently the treatment sites were tape stripped 20 times using D-Squame tape. The tape strips were saved for analysis. After tape stripping one 4 mm biopsy was taken from each site. The biopsies were delivered to DMPK for analysis of tissue concentration.

Bioanalysis by LC-MS/MS was performed at DMPK&Safety. Briefly, betamethasone dipropionate was extracted from skin biopsies using ether. The ether was evaporated and the residue was reconstituted in Methanol:Water (50:50) containing deteurated betamethasone dipropionate as internal standard. Tape strips were extracted using acetonitrile.

Samples were analysed using an AB Sciex API 5000.

Results

The amount of BDP in the samples were corrected for variation in area and expressed as $\mu g/cm^2$.

In the tape strips all compositions showed higher amounts of BDP at the early time points (2 h, 24 h) compared to the late time point. The tape strips from the fields treated with Formulation 2 showed the highest amounts of betamethasone dipropionate.

Figure 9:
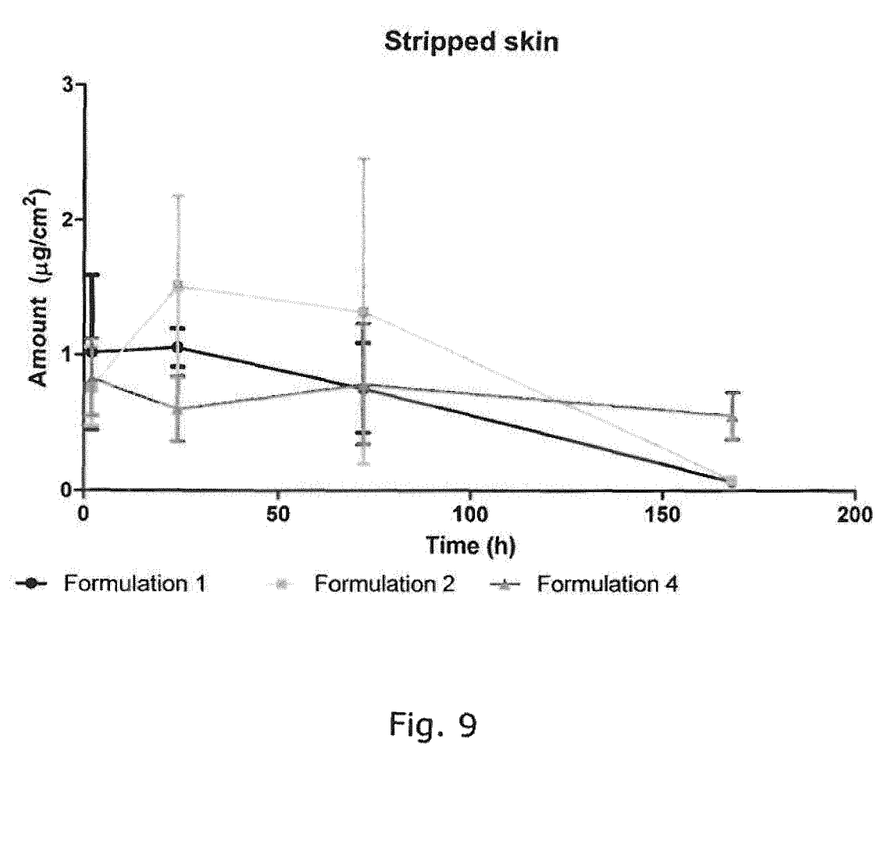
FIG. 9 is a graph showing the amount of active ingredient (BDP) in skin of hairless guinea pigs as a function of time after application of a film-forming composition containing Eudragit RS PO alone (formulation 1), Eudragit RS PO and tributyl citrate (formulation 2) and Eudragit RS PO, tributy citrate and 0.16% w/w MCT (formulation 4).

The results from tape stripped skin are shown in FIG. 9. The skin that had been tape stripped showed low amounts of BDP, reflecting that a large proportion of the dose was residing in the tape strips. However, skin treated with Formulation 4 had a less pronounced decrease in skin amounts over time. This may indicate a prolonged release from Formulation 4 relative to the other formulations. Skin treated with Formulation 2 showed the highest amounts in the tape stripped skin after 1-3 days, but after 7 days, skin treated with Formulations 1 and 2 showed similar amounts of Betamethasone dipropionate. Due to a high variability in the analysis of samples of stripped skin treated with formulation 5, data for that formulation are not presented.

Intact skin showed higher amounts of BDP than what was observed for the tape stripped skin (data not shown). This reflected the fact that a large proportion of the dose was residing in the stratum corneum. Skin treated with Formulation 2 showed the highest amounts of compound, and skin treated with Formulations 1, 4 and 5 showed lower amounts.

The amounts of BDP in the tape strips and in the non-stripped skin were similar, reflecting the fact that most of the dose resided in the stratum corneum. Formulation 2 showed the highest amount in both sample types at the early time points.

The skin that had been tape stripped showed low amounts of BDP. Skin treated with formulation 2 showed the highest amounts in the tape stripped skin after 1-3 days, but after 7 days, skin treated with formulations 1 and 2 showed similar amounts of BDP. However, skin treated with formulation 4 had a less pronounced decrease in skin amounts as a function of time. This may indicate a prolonged release from formulation 4 relative to the other formulations.

The invention claimed is:

1. A substantially anhydrous sprayable film-forming pharmaceutical composition for dermal application, the composition comprising:
    at least one therapeutically active ingredient dissolved in a pharmaceutically acceptable propellant mixture of dimethyl ether and a second propellant selected from the group consisting of $C_{3-5}$ alkanes and hydrofluoroalkanes, wherein the propellant is present in an amount of 50-99.5% w/w of the composition,
    a film-forming polymer in an amount of 0.1-50% w/w,
    a plasticizer in an amount of 0.1-10% w/w, and
    medium chain triglycerides as an oily release-enhancing agent in an amount of 0.1-15% w/w,
    wherein the composition is essentially free from a low-molecular volatile solvent.

2. A composition according to claim 1, wherein the film-forming polymer is selected from the group consisting of cellulose derivatives, acrylic polymers, acrylic copolymers, methacrylate polymers, methacrylate copolymers, polyurethanes, polyvinylalcohol or a derivative thereof such as polyvinylacetate, silicone polymers and silicone copolymers, or copolymers thereof.

3. A composition according to claim 2, wherein the cellulose derivative is selected from the group consisting of ethyl cellulose, methyl cellulose, hydroxyethyl cellulose, hydroxypropyl cellulose, hydroxypropylmethyl cellulose.

4. A composition according to claim 2, wherein the acrylic polymer is selected from the group consisting of methyl methacrylate and butyl methacrylate copolymer, ethyl acrylate and methyl methacrylate copolymer, acrylate and ammonium methacrylate copolymer type A and type B, and acrylates/octylacrylamide copolymer.

5. A composition according to claim 1, wherein the plasticizer is selected from the group consisting of triethyl citrate, tributyl citrate, acetyl triethyl citrate, triacetin, dibutyl sebacate and polyethylene glycol 100-1000.

6. A composition according to claim 1, wherein the second propellant $C_{3-5}$ alkane is selected from the group consisting of n-propane, isopropane, n-butane or isobutane.

7. A composition according to claim 6, wherein the $C_{3-5}$ alkane is n-butane and/or isobutane.

8. A composition according to claim 7, wherein the ratio of n-butane and/or isobutane to dimethyl ether is in the range of 6:1-0:1 v/v.

9. A composition according to claim 1 further comprising an anti-nucleating agent.

10. A composition according to claim 9, wherein the anti-nucleating agent is selected from the group consisting of polyvinyl alcohol, hydroxypropyl cellulose, hydroxypropylmethyl cellulose, methyl cellulose, polyvinylpyrrolidone and carboxymethyl cellulose.

11. A composition according to claim 1, wherein the therapeutically active ingredient is selected from the group consisting of vitamin D derivatives or analogues, corticosteroids, phosphodiesterase 4 inhibitors, ingenol derivatives, retinoids, JAK inhibitors, NK-1 receptor antagonists, calcineurin inhibitors, keratolytic agents, antibiotics, non-steroidal anti-inflammatory agents and local anesthetics.

12. A composition according to claim 11 comprising calcipotriol or calcipotriol monohydrate as the vitamin D analogue and betamethasone dipropionate or valerate as the corticosteroid.

13. A pressurized container adapted to dispensing a topical composition on an affected skin area, the container including a container body comprising a composition according to claim 1 and a valve assembly including an actuator for releasing the composition as a spray.

14. A container according to claim 13, wherein the valve assembly contains at least one aperture with a diameter of 0.05-1 mm.

15. A container according to claim 13, wherein the actuator is provided with an orifice with a diameter of 0.3-1.5 mm.

16. A method of treating dermatological diseases or conditions, wherein the method comprises applying a therapeutically effective amount of the composition of claim 1 on to the skin of a patient in need of treatment.

17. The method of claim 16, wherein the dermatological disease or condition is selected from the group consisting of psoriasis, pustulosis palmoplantaris, ichtyosis, atopic dermatitis, contact dermatitis, eczema, actinic keratosis, pruritus, rosacea and acne.

18. A composition according to claim 7, wherein the ratio of n-butane and/or isobutane to dimethyl ether is in the range of 4:1-1:1.

19. A composition according to claim 7, wherein the ratio of n-butane and/or isobutane to dimethyl ether is in the range of 4:2-1:1.

20. A composition according to claim 1, wherein the therapeutically active ingredient is selected from the group consisting of vitamin D derivatives or analogues, corticosteroids, phosphodiesterase 4 inhibitors, ingenol derivatives, adapalene, JAK inhibitors, NK-1 receptor antagonists, tacrolimus, pimecrolimus, salicylic acid, lactic acid, fusidic acid, clindamycin, non-steroidal antiinflammatory agents and lidocain.

* * * * *